United States Patent [19]

Smith et al.

[11] Patent Number: 6,127,370
[45] Date of Patent: Oct. 3, 2000

[54] METHOD FOR TREATING ALZHEIMER'S DISEASE

[75] Inventors: Anthony David Smith, Iffley; Kim Anthony Jobst, Glasgow, both of United Kingdom

[73] Assignee: Bristol-Myers Squibb Company, Princeton, N.J.

[21] Appl. No.: 09/435,804

[22] Filed: Nov. 8, 1999

Related U.S. Application Data

[62] Division of application No. 08/959,035, Oct. 28, 1997, Pat. No. 6,008,221.
[60] Provisional application No. 60/030,642, Nov. 6, 1996.
[51] Int. Cl.$^7$ ................................................. A61K 31/505
[52] U.S. Cl. .......................................... 514/252; 514/258
[58] Field of Search ...................................... 514/254, 258

[56] References Cited

FOREIGN PATENT DOCUMENTS

0595005A1   5/1994   European Pat. Off. .

OTHER PUBLICATIONS

McCully, K.S., "Homocysteine and vascular disease", Mature Med., 1996; 2:386–389.

Blundell, G. et al., "Homocysteine mediated endothelial cell toxicity and its amelioration", Atherosclerosis, 1996; 122:163–172.

Stamler, J.S. et al, "Biological Chemistry of Thiols in the Vasculature and in Vascular–related Disease", Nutr. Rev., 1996; 54:1–30.

Brattstrom, L.E. et al, "Moderate Homocysteinemia—A Possible Risk Factor For Arteriosclerotic Cerebrovascular Disease", Stroke, 1984; 15:1012–6.

Brattstrom, L. et al, "Hyperhomocysteinaemia in stroke: prevalence, cause, and relationships to type of stroke and stroke risk factors", Eur. J. Clin. Invest., 1992; 22:214–221.

Boushey, C.J. et al, "A quantitative Assessment of Plasma Homocysteine as a Risk Factor for Vascular Disease", J. Am. Med. Assoc., 1995; 274:1049–1057.

Ubbink, J.B. et al, "Vitamin Requirements for the Treatment of Hyperhomocysteinemia in Humans", J. Nutr., 124:1927–1933.

Wulfert, E., "Treatament Development Strategies for Alzheimer's Disease", European J. Medicinal Chemistry 30(Suppl): 148s–162s.

Young, J.B., "Angiotensin–Converting Enzyme Inhibitors Post–Myocardial Infarction", Cardiology Clinics, vol. 13, No. 3, Aug. 1995, pp. 379–390.

Frosst, P., et al, "A candidate genetic risk factor for vascular disease: a common mutation in methylenetetrahydrofolate reductase", Nature Genetics, vol. 10, May 1995, pp. 111–113.

Barnes, N.M., et al, "Angiotensin converting enzyme density is increased in temporal cortex from patients with Alzheimer's disease", Europ. J. of Pharmacology, 200(1991) 289–292.

Lansbury, P.T., Jr., "Consequences of the Molecular Mechanism of Amyloid Formation for the Understanding of the Pathogenesis of Alzheimer's Disease and the Development of Therapeutic Strategies", Arzneimittel–Forschung, 1995, 45(3A): 452–434.

Takeda, H., et al, "Protective Effect of the Angiotensin–Converting Enzyme Inhibitor Captopril on Postischemic Myocardial Damage in Perfused Rat Heart", Jpn. Circ. J., 1997; 61:687–694.

Ishibashi, Y., et al, "The Nitric Oxide Donor ITF 1129 Augments Subendocardial Blood Flow During Exercise–Induced Myocardial Ischemia", J. of Cardiovascular Pharmacology, vol. 30, No. 3, pp. 374–382.

Piana, R.N., et al, "Angiotensin–Converting Enzyme Inhibition Preserves Endothelium–Dependent Coronary Microvascular Responses During Short–term Ischemia–Reperfusion", Circulation, 1996, vol. 93, No. 3, pp. 544–551.

Munzel, T., et al, "Long–term Angiotensin–Converting Enzyme Inhibition With High–Dose Enalapril Retards Nitrate Tolerance in Large Epicardial Arteries and Prevents Rebound Coronary Vasoconstrictin *In Vivo*", Circulation, 1996; 93:2052–2058.

Birincioglu, M., et al, "Protective Effect of ACE Inhibitors on Ischemia–Reperfusion–induced Arrhythmias in Rats: Is this Effect Related to the Free Radical Scavenging Action of these Drugs?", Free Rad. Res. vo. 27(4) pp. 389–396 (1997).

Ii, Kunio, "The Role of β–Amyloid in the Development of Alzheimer's Disease", Drugs & Aging 7(2):97–109, (1995).

Plosker, G.L., et al, "Captopril A Review of its Pharmacology and Therapeutic Efficacy After Myocardial Infarction and in Ischaemic Heart Disease", Drugs & Aging 7(3); 226–253 (1995).

Buee, L. et al, "Pathological alterations of the cerebral microvasculature in Alzheimer's disease and related dementing disorders", Acta Neuropathol (1994) 84:469–480.

Boushey, C.J. et al, "A Quantitative Assessment of Plasma Homocysteine as a Risk Factor for Vascular Disease", J. Am. Med. Assoc. 1995, vol. 274, 1049–1057.

Nygard, O. et al, "Total Plasma Homocysteine and Cardiovascular Risk Profile", J. Am. Med. Assoc., 1995, vol. 274, 1526–1533.

Riggs, K.M. et al, "Relations of vitamin B–12, vitamin B–6, folate, and homocysteine to cognitive performance in the Normative Aging Study", Am. J. Clin. Nutr., 1996;63:306–314.

(List continued on next page.)

*Primary Examiner*—Theodore J. Criares
*Attorney, Agent, or Firm*—Burton Rodney

[57] ABSTRACT

A method is provided for treating occlusive vascular disease or Alzheimer's disease, wherein the patient has at least moderately elevated blood levels of homocysteine and at least moderately reduced blood levels of folate and vitamin $B_{12}$, wherein the patient is treated with folic acid, a folate or a derivative thereof, and optionally vitamin $B_{12}$, and optionally an organic nitrate such as isosorbide mononitrate or dinitrate, or an ACE inhibitor or an angiotensin II antagonist, or a NEP/ACE inhibitor or a combination of two or more of the above.

16 Claims, 1 Drawing Sheet

OTHER PUBLICATIONS

Renvall, M.J. et al, "Nutritional Status of Free–Living Alzheimer's Patients", Am. J. Med. Sci, 1989;298:20–27.

Cole, M.G. et al, "Low Serum Vitamin $B_{12}$ in Alzheimer–Type Dementia", Age Ageing, 1984, 13:101–105.

Karnaze, D.S. et al, "Low Serum Cobalamin Levels in Primary Degenerative Dementia", Arch. Intern. Med., 1987;147:429–431.

Nijst, T.Q. et al, "Vitamin B12 and folate concentrations in serum and cerebrospinal fluid of neurological patients with special reference to multiple sclerosis and dementia", J. Neurol. Neurosurg. Psychiatry, 1990; 53:951–954.

Beal, M.F. et al, "Neurochemical Characterization of Excitotoxin Lesions in the Cerebral Cortex", J. Neurosci., 1991; 11:147–158.

Bottiglieri, T. et al, "The Clinical Potential of Ademetionine (S–Adenosyl–methionine) in Neurological Disorders", Drugs, 1994; 48:137–152.

Bird, A.P., "Functions for DNA Methylation in Vertebrates", Cold Spring Harb Symp Quant Biol, 1993; 58:281–285.

Mullaart, E. et al, "Increased Levels of DNA Breaks in Cerebral Cortex of Alzheimer's Disease Patients", Neurobiol Aging, 1990; 11:169–173.

Clark, R.F. et al, "The structure of the presenilin 1 (S182) gene and identification of six novel mutations in early onset AD families", Nat. Genet, 1995; 11:219–222.

Stampfer, M.J. et al, "Folate and Cardiovascular Disease: Why We Need a Trial Now", J. Am. Med. Assoc., 1996; 275:1929–1930.

Rolland, P.H. et al, "Hyperhomocysteinemia–Induced Vascular Damage in the Minipig. Captopril–Hydrochlorthiazide Combination Prevents Elastic Alterations", Circulation, 1995; 91:1161–1174.

METHOD FOR TREATING ALZHEIMER'S DISEASE

This application is a Division of Ser. No. 08/959,035, filed Oct. 28, 1997, now U.S. Pat. No. 6,008,221, which claims the benefit of U.S. Provisional Application No. 60/030,642 filed Nov. 6, 1996.

FIELD OF THE INVENTION

The present invention relates to a method for inhibiting or preventing microvascular events leading to ischemia and/or neurodegeneration, such as in occlusive vascular disease, or in Alzheimer's disease, wherein the patient has at least moderately elevated blood levels of homocysteine and at least moderately reduced blood levels of folate and vitamin $B_{12}$.

BACKGROUND OF THE INVENTION

Alzheimer's disease (AD) may be triggered by a series of microvascular ischemic events in the brain, notably in the medial temporal lobe. These events lead to localized hypoxia and perhaps hypoglycemia which in turn lead to the formation of neurofibrillary tangles in vulnerable neurons of the hippocampal formation. The deposition of these tangles leads eventually to death of the neurons and thus the loss of synaptic connections between neurons within the medial temporal lobe and between neurons of the medial temporal lobe and neurons in the neocortex. It is the loss of these neuronal connections that leads to the symptoms of AD.

The above is supported by the following.

In addition to the well-known amyloid angiopathy, small blood vessels in the brain in AD show several abnormalities that could lead to a decrease in blood flow, notably a reduced density, reduced diameter, a disorganized angioarchitecture ((1) de la Torre and Mussivand, 1993; (2) Kalaria, 1992), and a loss of endothelium ((3) Kalaria and Hedera, 1995), which are particularly prominent in the hippocampus ((4) Fischer et al, 1990).

It is notable that the microvascular abnormalities found in the hippocampus in AD are especially prominent in area CA1 ((5) Buee et al, 1994), since the same area of the hippocampus is especially vulnerable to hypoxia ((6) Schmidt-Kastner and Freund, 1991) and is the part of the hippocampus that shows the greatest density of neurofibrillary tangles ((7) Ball et al, 1985), and the greatest cell loss ((8) West et al, 1994) in AD.

It is believed that one of the causes of the microvascular events leading to ischemia in the medial temporal lobe is a moderate deficiency in folate and vitamin $B_{12}$ which, in turn, lead to an elevation of plasma total homocysteine levels. It is the toxic effect of homocysteine on the blood vessels that initiates the pathological cascade process leading to changes in the microvasculature.

Thus, the microvascular abnormalities found in AD could be brought about by chronic exposure to elevated levels of plasma homocysteine, which causes disorganization of the elastic lamina ((9) Rolland et al, 1995) and damage to the endothelium ((10) McCully, 1996; (11) Rose and Tudball, 1996; (12) Stamler and Slivka, 1996) in arterioles in the periphery. Small blood vessels in the brain are likely to be particularly sensitive to the toxic effect of homocysteine on the elastic fibers since cerebral vessels only have a single elastic lamina. A correlation has been found between elevated homocysteine and the risk of cerebrovascular disease such as arteriosclerotic cerebrovascular disease and stroke ((13) Brattstrom et al, 1984; (14) Brattstrom et al, 1992).

It has now been found that patients with histopathologically-confirmed Alzheimer's disease have elevated levels of serum total homocysteine. It has also been found that the raised serum level of homocysteine in Alzheimer patients is associated with reduced serum levels of two vitamins, folate and vitamin $B_{12}$, that are required as co-factors in the conversion of homocysteine to methionine. It appears that the elevated homocysteine is due to a deficiency in the dietary intake or in the bioavailability of folic acid and vitamin $B_{12}$.

It is also known that blood levels of homocysteine may be lowered by treatment with high doses of folate ((15) Boushey et al, 1995, (16) Stampfer and Rimm, 1996; (17) Ubbink et al, 1994).

Angiotensin-converting enzyme (ACE) inhibitors, such as captopril, fosinopril, enalapril, ceronapril, lisinopril and the like, and angiotensin II antagonists such as losartan, irbesartan, valsartan, candesartan, tasosartan and eprosartan, are known for their use as vasodilating cardiovascular agents in treating high blood pressure and congestive heart failure.

Nitrates such as isosorbide dinitrate, isosorbide mononitrate and nitroglycerin are known for their coronary and peripheral vasodilating effect in the prevention and treatment of angina pectoris. They have been shown in clinical studies to limit infarct size.

DESCRIPTION OF THE INVENTION

In accordance with the present invention, a method is provided for inhibiting microvascular events leading to ischemia and/or neurodegeneration, as in occlusive vascular disease, both cerebral and peripheral, or in Alzheimer's disease, wherein the patient has at least moderately elevated blood levels of homocysteine and at least moderately reduced blood levels of folate and vitamin $B_{12}$. The method of the invention includes the step of administering to such patient a therapeutically effective amount of a drug which causes a reduction in blood levels of homocysteine (an established risk factor for vascular disease (15) Boushey et al, 1995), and/or modifies the toxic effects of homocysteine on the vasculature or on nerve cells in the brain, to inhibit progression of Alzheimer's disease.

In treating Alzheimer's disease, it is preferred that the drug administered to lower the blood level of homocysteine is folic acid or a folate or a derivative thereof (as defined hereinafter) or a combination of two or more thereof alone, or optionally with vitamin $B_{12}$ (in order to avoid the risk of neuropathy, (18) Savage and Lindenbaum, 1995). However, any drug which lowers the blood level of homocysteine may be employed such as betaine or vitamin $B_6$ or a combination thereof of with any of the above drugs used to lower serum homocysteine, optionally with vitamin $B_{12}$.

Furthermore, in treating Alzheimer's disease, modifying the effects of homocysteine on the vasculature or nerve cells in the brain can be achieved in two ways. First, by administration of nitric oxide donors ((12) Stamler and Slivka, 1996), such as organic nitrates (e.g. isosorbide mono- or dinitrate) since it appears that natural detoxification of homocysteine is achieved by nitric oxide generated in the endothelium ((19) Stamler et al, 1993). Second, by administration of ACE-inhibitors, angitensin II antagonists or NEP/ACE inhibitors. ACE inhibitors which have been shown to reduce the damage to the endothelium and to the elastic laminae in arterioles caused by homocysteine ((20) Charpiot et al, 1993; (9) Rolland et al, 1995). Although the exact mechanisms by which ACE-inhibitors reduce the toxic effects of homocysteine are not known, it is theorized that they may, in part, involve nitric oxide. ACE-inhibitors have two actions that increase local nitric oxide formation by the microvascular endothelium. 1) ACE-inhibitors potentiate the response of the endothelium to agonists that increase the release of endothelium-derived relaxing factors, such as nitric oxide (U.S. Pat. No. 5,212,165, Aberg and Ondetti, 1989; (21) Rizzoni et al, 1995). 2) ACE-inhibitors increase the local levels of kinins, such as bradykinin, which are stimulants of nitric oxide formation by the endothelium ((22) Hartman, 1995; (23) Linz et al, 1995).

It is preferred that in treating Alzheimer's disease, the drug administered to counteract or modify the toxic effects of homocysteine on the vasculature or on nerve cells in the brain is a nitric oxide donor, or an ACE inhibitor or an angiotensin II antagonist or NEP/ACE inhibitor or a combination of two or more of the above or a combination of one or more of the above with folic acid, folate or a derivative thereof, betaine or vitamin $B_6$, (or a combination of two or more thereof) alone or in combination with vitamin $B_{12}$.

In treating occlusive vascular disease, it is preferred that (1) the drug administered to lower the blood level of homocysteine is folic acid or a folate or a derivative thereof or betaine or vitamin $B_6$ or a combination of two or more thereof, alone, or optionally with vitamin $B_{12}$, and (2) the drug administered to modify the effects of homocysteine on the vasculature or on nerve cells in the brain is folic acid or a folate or a derivative thereof, betaine or vitamin $B_6$ or a combination of two or more thereof, alone, or in combination with vitamin $B_{12}$ and/or in combination with a nitric oxide donor, ACE inhibitor, or an angiotensin II antagonist or a NEP/ACE inhibitor or a combination of two or more of the above.

BRIEF REFERENCE TO FIGURES

FIG. 1 depicts cumulative frequency distribution plots of serum folate concentrations for confirmed Alzheimer patients, patients with unconfirmed Alzheimer's disease (dementia of Alzheimer type, DAT) and Controls and shows a shift in the distribution of folate concentrations in Alzheimer cases to lower values compared with controls; and FIG. 2 depicts cumulative frequency distribution plots of serum homocysteine for confirmed Alzheimer patients, patients with unconfirmed Alzheimer's disease (DAT) and Controls and shows a shift in the distribution of homocysteine to higher values compared with controls.

DETAILED DESCRIPTION OF THE INVENTION

Figure 1:
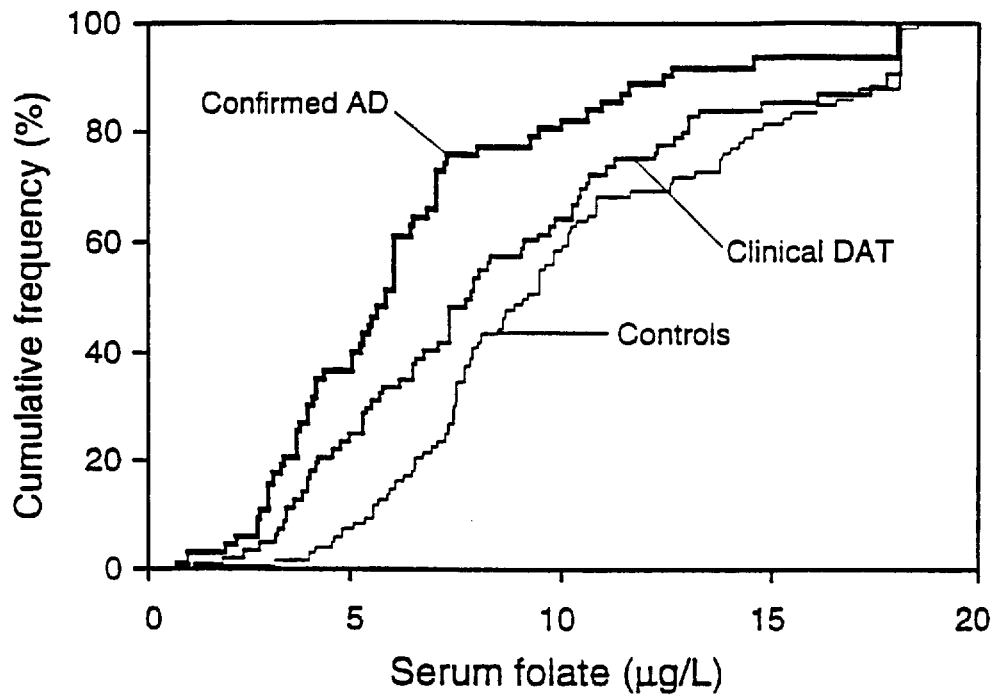

The phrase "at least moderately elevated blood levels of homocysteine" refers to a serum homocysteine level in the upper tertile for controls of the same age or at least about 15% higher than the homocysteine blood levels of controls of the same age.

The phrase "at least moderately reduced blood levels of folate" refers to a serum folate level in the lower tertile for controls of the same age or at least about 15% lower than folate blood levels of controls of the same age.

The phrase "at least moderately reduced blood levels of vitamin $B_{12}$" refers to a serum vitamin $B_{12}$ level in the lower tertile for controls of the same age or at least about 15% lower than vitamin $B_{12}$ blood levels of controls of the same age.

The term "occlusive vascular disease" encompasses stroke, TIA, intermittent claudication, vascular dementia, multi-infarct dementia, senile onset dementias, presenile dementias or Binswanger's disease.

In accordance with the present invention, the blood levels of homocysteine can be lowered or the toxic effect of homocysteine can be modified through administration of a therapeutically effective amount of folic acid (pteroylmonoglutamate) or one or more folylpolyglutamates as well as compounds in which the pyrazine ring of the pterin moiety of folic acid or of the folylpolyglutamates is reduced to give dihydrofolates or tetrahydrofolates, as well as derivatives of all the preceding compounds in which the N-5 or N-10 positions carry one carbon units at various levels of oxidation. Thus, examples of compounds suitable for use herein to lower blood levels of homocysteine, or treat the toxic effects of homocysteine, include, but are not limited to folic acid (pteroylmonoglutamate),
dihydrofolate, tetrahydrofolate,
5-methyltetrahydrofolate,
5,10-methylenetetrahydrofolate,
5,10-methenyltetrahydrofolate,
5,10-formiminotetrahydrofolate,
5-formyltetrahydrofolate (leucovorin), and
10-formyltetrahydrofolate.
Preferred is folic acid.

The angiotensin converting enzyme inhibitor which may be employed herein to modify the toxic effects of homocysteine includes those containing a mercapto (-S-) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol. 10:131 (1983); as well as pivopril, that is

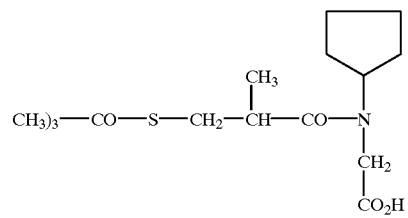

and YS980, that is

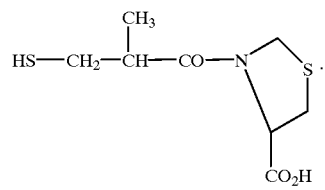

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)-phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Nos. 80822 and 60668; Chugai's MC-838 disclosed in CA. 102:72588v and Jap. J. Pharmacol. 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Patent No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacol. 9:39 (1987); $R_o$ 31-2201 (Hoffman-LaRoche), disclosed in FEBS Lett. 165:201 (1984); lisinopril (Merck), indalapril (delapril) disclosed in U.S. Pat. No. 4,385,051; indolapril (Schering) disclosed in J. Cardiovasc. Pharmacol. 5:643, 655 (1983), spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI 925 (Warner-Lambert) ([3S-[2[R(*)R(*)]] 3R(*)]-2-[2-[[1-(ethoxy-carbonyl)-3-phenylpropyl]amino[-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

Preferred ACE inhibitors are captopril, as well as fosinopril, enalapril, lisinopril, quinapril, benazepril, fentiapril, ramipril, and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, U.S. application Ser. No. 160,540, filed Dec. 1, 1993 (file HA599b), U.S. Pat. No. 5,504,080, U.S. application Ser. No. 487,358, filed Jun. 7, 1995 (file HA662b), U.S. Pat. No. 5,525,723, European Patent Application 0599,444, 0481, 522, 0599,444, 0595,610, European Patent Application 0534363A2, 534,396 and 534,492, and European Patent Application 0629627A2.

Preferred are those NEP/ACE inhibitors which are designated as preferred in the above patents/applications which U.S. patents/applications are incorporated herein by reference.

The angiotensin II receptor antagonist (also referred to herein as angiotensin II antagonist or AII antagonist) suitable for use herein to modify the toxic effects of homocysteine includes, but is not limited to, irbesartan, losartan, valsartan, candesartan, tasosartan or eprosartan, with irbesartan or losartan being preferred.

The nitric oxide donor employed to modify the toxic effects of homocysteine includes, but is not limited to, organic nitrates such as isosorbide-5-mononitrate, isosorbide dinitrate, nitroglycerin, with isosorbide-5-mononitrate being preferred.

Preferred combinations of ACE inhibitor or AII antagonist and nitrate are captopril or fosinopril, or losartan or irbesartan in combination with isosorbide-5-mononitrate and/or folic acid and/or vitamin $B_{12}$.

The folic acid of folate will be employed in a weight ratio to vitamin $B_{12}$ (where employed) of within the range from about 0.1:1 to about 50:1 and preferably from about 0.2:1 to about 25:1.

The nitrate (where employed) in combination with an ACE inhibitor or AII antagonist, will be in a weight ratio to ACE inhibitor or AII antagonist or NEP/ACE inhibitor of within the range from about 0.1:1 to about 50:1, and preferably from about 0.2:1 to about 20:1.

It will also be appreciated that the drugs or compounds employed herein in accordance with the present invention may be employed in conjunction or combination with one or more known therapeutic agents for treating Alzheimer's disease, such as, for example, but not limited to cholinesterase inhibitors such as tacrine, muscarinic receptor agonists, inhibitors of β-amyloid production, and/or inhibitors of neurofibrillary tangle formation.

In carrying out the method of the present invention, the various compounds to be administered in accordance with the present invention, such as folic acid, folate or derivative thereof, betaine or vitamin $B_6$, vitamin $B_{12}$, nitric oxide donor, ACE inhibitor or AII antagonist or NEP/ACE inhibitor may be administered to humans incorporated in a conventional systemic dosage form, such as a tablet, capsule, elixir or injectable. The above dosage forms will also include the necessary carrier material, excipient, lubricant, buffer, antibacterial, bulking agent (such as mannitol), antioxidants (ascorbic acid or sodium bisulfite) or the like. Oral dosage forms are preferred for the above drugs including vitamins although parenteral forms such as subcutaneous, intramuscular, intraperitoneal, and intravenous are quite satisfactory as well.

The dose administered must be carefully adjusted according to age, weight and condition of the patient, as well as the route of administration, dosage form and regimen and the desired result.

In carrying out the method of the invention, the folic acid or folate or derivative, betaine or vitamin $B_6$ will be employed in daily oral doses within the range from about 0.1 to about 100 mg, preferably from about 2 to about 10 mg, and vitamin $B_{12}$ will be employed in daily oral doses within the range from about 0.001 mg to about 10 mg, preferably from about 0.5 to about 2.5 mg.

For parenteral administration, the folic acid, folate or derivative thereof, betaine or vitamin $B_6$ will be employed in an amount within the range from about 0.002 mg/kg to about 10 mg/kg, and preferably from about 0.01 mg/kg to about 3 mg/kg and the vitamin $B_{12}$ will be employed in an amount within the range from about 0.002 mg/kg to about 5 mg/kg, and preferably from about 0.01 mg/kg to about 3 mg/kg.

For oral administration, a satisfactory result may be obtained employing the ACE inhibitor or AIII antagonist or NEP/ACE inhibitor in an amount within the range of from about 0.01 mg/kg to about 100 mg/kg, and preferably from about 0.1 mg/kg to about 25 mg/kg. The nitric oxide donor will be employed in an amount within the range of from about 0.01 mg/kg to about 100 mg/kg and preferably from about 0.1 mg/kg to about 25 mg/kg.

The above drugs (including vitamins) may be employed together in the same oral or parenteral dosage forms or in separate oral and parenteral dosage forms taken at the same time.

A preferred oral dosage form, such as tablets or capsules, will contain the ACE inhibitor or AII antagonist in an amount within the range from about 0.1 to about 500 mg, preferably from about 5 to about 200 mg, and more preferably from about 10 to about 150 mg; the nitric oxide donor will be present in an amount from about 1 to about 350 mg, preferably from about 2 to about 200 mg, and more preferably from about 30 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg, and the nitric oxide donor in an amount within the range from about 0.005 to about 20 mg/kg, and preferably from about 0.01 to about 2 mg/kg.

Where a drug is to be administered intravenously, it will be formulated in conventional vehicles, such as distilled water, saline, Ringer's solution or other conventional carriers.

It will be appreciated that preferred dosages of ACE inhibitor, AII antagonist and organic nitrates will be as set out in the latest edition of the Physician's Desk Reference (PDR).

The compositions described above may be administered in the dosage forms as described above in single or divided doses of one to four times daily. It may be advisable to start a patient on a low dose (combination) and work up gradually to a high dose (combination).

Tablets of various sizes can be prepared, e.g., of about 10 to 1000 mg in total weight, containing one or more of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonsful.

Such dosage forms can be administered to the patient on a regimen of one to four doses per day.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of folic acid, folate or derivative thereof, betaine or vitamin $B_6$ and vitamin $B_{12}$; ACE inhibitor, or AII antagonist or organic nitrate, and folic acid, folate of derivative thereof, betaine or vitamin $B_6$ and optionally vitamin $B_{12}$; or nitrate and ACE inhibitor or AII antagonist or NEP/ACE inhibitor are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Many of the active substances described above form commonly known, pharmaceutically acceptable salts such as alkali metal and other common basic salts or acid addition salts, etc. References to the base substances are therefore intended to include those common salts known to be substantially equivalent to the parent compound.

REFERENCES (1) de la Torre, J. C. and Mussivand, T. (1993) - Can disturbed brain microcirculation cause Alzheimer's disease. Neurological Research 15, 146–153.

(2) Kalaria, R. N. (1992) - The blood brain barrier and cerebral microcirculation in Alzheimer disease. Cerebrovasc. Brain Metab. Rev. 4, 226–260.

(3) Kalaria, R. N. and Hedera, P. - (1995) Differential degeneration of the cerebral microvasculature in Alzheimer's disease. Neuroreport 6, 477–480.

(4) Fischer, V. W., et al (1990) - Altered Angioarchitecture in Selected Areas of Brains with Alzheimer's Disease. Acta Neuropathologica 79, 672–679.

(5) Buee, L., et al (1994) - Pathological alterations of the cerebral microvasculature in Alzheimer's disease and related dementing disorders. Acta Neuropathol, Berl 87, 469–480.

(6) Schmidt-Kastner, R. and Freund, T. F. (1991) - Selective vulnerability of the hippocampus in brain ischemia. Neuroscience 40, 599–636.

(7) Ball, M. J., et al (1985) - A new definition of Alzheimer's disease: a hippocampal dementia. Lancet i, 14–16.

(8) West, M. J., et al (1994) - Differences in the pattern of hippocampal neuronal loss in normal aging and Alzheimer's disease. Lancet 344, 769–772.

(9) Rolland, P. H., et al (1995) - Hyperhomocysteinemia-induced vascular damage in the minipig. Captopril-hydrochlorothiazide combination prevents elastic alterations. Circulation 91, 1161–74.

(10) McCully, K. S. (1996) - Homocysteine and vascular disease. Nature Med. 2, 386–389.

(11) Rose, F. and Tudball, N. (1996) - Homocysteine mediated endothelial cell toxicity and its amelioration. Atherosclerosis 122, 163–172.

(12) Stamler, J. S. and Slivka, A. (1996) - Biological chemistry of thiols in the vasculature and in vascular-related diseases. Nutr. Rev. 54, 1–30.

(13) Brattstrom, L. E., et al (1984) - Moderate homocysteinemia—a possible risk factor for arteriosclerotic cerebrovascular disease. Stroke 15, 1012-6.

(14) Brattstrom, L. E., et al (1992) - Hyperhomocysteinaemia in stroke: prevalence, cause, and relationships to type of stroke and stroke risk factors. Eur. J. Clin. Invest. 22, 214-21.

(15) Boushey, C. J., et al (1995) - A quantitative assessment of plasma homocysteine as a risk factor for vascular disease. Probable benefits of increasing folic acid intakes. J. Am. Med. Assocn. 274, 1049-57.

(16) Stampfer, M. J. and Rimm, E. (1996) - Folate and cardiovascular disease: why we need a trial now. J. Am. Med. Assocn. 275, 1929–1930.

(17) Ubbink, J. B., et al (1994) - Vitamin requirements for the treatment of hyperhomocysteinemia in humans. J. Nutr. 124, 1927-33.

(18) Savage, D. and Lindenbaum, J. (1995) - Folate-cyanocobalamin interactions. In: Folate in health and disease, pp. 237–285. Ed. L. Bailey. Marcel Dekker: New York.

(19) Stamler, J. S., Osborne, J. A., Jaraki, O., Rabbani, L. E., Mullins, M., Singel, D. and Loscalzo, J. (1993) - Adverse vascular effects of homocysteine are modulated by endothelium-derived relaxing factor and related oxides of nitrogen. J Clin Invest 91, 308-18.

(20) Charpiot, P., Rolland, P. H., Friggi, A., Piquet, P., Scalbert, E., Bodard, H., Barlatier, A., Latrille, V., Tranier, P., Mercier, C. and et al (1993) - ACE inhibition with perindopril and atherogenesis-induced structural and functional changes in minipig arteries. Arterioscler Thromb 13, 1125-38.

(21) Rizzoni, D., Castellano, M., Porteri, E. Bettoni, G., Muiesan, M. L., Cinelli, A. and Rosei, E. A. (1995) - Effects of low and high doses of fosinopril on the structure and function of resistance arteries. Hypertension 26, 118-23.

(22) Hartman, J. C. (1995) - The role of bradykinin and nitric oxide in the cardioprotective action of ACE inhibitors. Ann Thorac Surg 60, 789-92.

(23) Linz, W., Wiemer, G., Gohlke, P., Unger, T. and Scholkens, B. A. (1995) - Contribution of kinins to the cardiovascular actions of angiotensin-converting enzyme inhibitors. Pharmacol Rev 47, 25–49.

The following Examples represent preferred embodiments of the present invention.

EXAMPLE 1

Folic acid tablets or capsules containing 5 mg folic acid (and prepared employing conventional pharmaceutical techniques), and vitamin $B_{12}$ tablets (1 mg) may be administered as a combination in accordance with the teachings of the present invention to inhibit progression of Alzheimer's disease. In addition, the folic acid and/or vitamin $B_{12}$ tablets may be ground up into powders and used together in a single capsule.

It will be appreciated that the folic acid tablets or capsules may be replaced with tablets or capsules containing folate or derivative thereof, betaine or vitamin $B_6$.

EXAMPLE 2

ACE inhibitor tablets such as captopril, enalapril, lisinopril, quinapril, or benzapril or a NEP/ACE inhibitor as disclosed in U.S. pat. applications Ser. Nos. 160,540 or 487,358, or an AII antagonist such as losartan or irbesartan may be employed alone or isosorbide-5-mononitrate tablets (5 mg) or isosorbide dinitrate tablets (10 mg) may be employed alone or the ACE inhibitor or AII antagonist or NEP/ACE inhibitor may be employed in combination with the organic nitrate or folic acid or folate or derivative thereof or betaine or vitamin $B_6$ (and vitamin $B_{12}$) for inhibiting progression of Alzheimer's disease.

EXAMPLE 3

The following experiments were carried out to measure serum total homocysteine and serum folate and vitamin $B_{12}$ in Alzheimer patients.

Background

Alzheimer's disease is associated with rapid atrophy of the medial temporal lobe, suggesting that an event in the brain, possibly microvascular ischaemia, might trigger the death of neurons. Hyperhomocysteinemia is an established risk factor for cardiovascular disease, and thus could be relevant to Alzheimer's disease.

Methods

The association between sporadic Alzheimer's disease and serum total homocysteine and its biological determinants (folate and vitamin $B_{12}$) at presentation in a case-control study of 76 cases with a histopathological diagnosis of Alzheimer's disease and 108 controls was examined.

Results

Serum homocysteine was significantly higher and serum folate and vitamin $B_{12}$ were significantly lower in confirmed Alzheimer's disease cases than in controls. The odds ratio of confirmed Alzheimer's disease associated with a homocysteine concentration in the top third ($\geq 14$ μmol/l) compared with the bottom third ($\leq 11$ μmol/l) of the control population, was 4.5 (95% Cl: 2.2–9.2) after adjustment for age, sex, social class, cigarette smoking and apolipoprotein-E ϵ4. For vitamin concentrations in the lower third compared with the upper third of the control population the adjusted odds ratio of Alzheimer's disease was 3.3 (95% Cl: 1.8–6.3) for serum folate and was 4.3 (95% Cl: 2.8–8.8) for Vitamin $B_{12}$. All three risk associations were independent of apolipoprotein-E ϵ4.

In a 3-year follow-up of 155 patients with a clinical diagnosis of dementia of the Alzheimer's type (DAT), medial lobe atrophy, as assessed by cat scan (CT) progressed more rapidly among those with higher homocysteine levels at presentation.

Interpretation

In this population, serum total homocysteine and low serum folate and vitamin $B_{12}$ are associated with Alzheimer's disease.

Introduction

Alzheimer's disease (AD) already affects about one in 50 adults in developed countries and its prevalence will grow with increasing life expectancy. The disease is characterized by the degeneration of neurons in the cerebral cortex, notably in the hippocampus, and it is likely to be irreversible.

Changes in the brain in sporadic AD can be distinguished from those associated with an acceleration of normal aging by alterations of specific neuronal proteins,[1,2] by the selective loss of certain groups of neurons in the hippocampus[3] and by the very rapid atrophy of the medial temporal lobe.[4] The latter finding led to the suggestion that the onset of AD follows a catastrophic event or critical insult to this vulnerable region of the brain in susceptible individuals.[4] In searching for a possible trigger of that event, the hypothesis that localized microvascular ischaemia is one of the triggers for the formation of neurofibrillary tangles in, and the eventual death of, neurons in the medial temporal lobe in AD was considered. In the hippocampus, the pyramidal neurons that show the highest density of tangles are those in area CA1[5]. These same neurons are severely depleted in AD, but not in normal aging.[3] Since the pyramidal neurons of area CA1 are also selectively vulnerable to hypoxia,[6] it is noteworthy that abnormalities in the cerebral microvasculature in AD that could lead to a reduction in local blood flow, such as a reduced density and diameter of small vessels and a disorganized angioarchitecture,[7,8] are particularly prominent in area CA1 of the hippocampus.[9] Consistent with a microvascular aetiology is the fact that the ε4 allele of apolipoprotein-E (ApoE) is not only a powerful risk factor for AD, but is also a risk factor for cardiovascular disease.[10] Thus some environmental factor may interact with a genetic susceptibility to initiate a cascade of microvascular ischaemia leading to neuronal death in the hippocampus.

Homocysteine is a reactive sulphur-containing amino acid present in plasma. Moderately elevated levels of plasma total homocysteine (tHcy) have been linked to increased risks of vascular disease's and neural tube defects.[12] Such moderately elevated levels of tHcy may reflect genetic defects, or deficiencies of nutritional factors required for homocysteine metabolism (folate and vitamin $B_{12}$), which are common in the population and increase with age.[13] A case-control study of histopathologically confirmed AD was carried out: firstly, to examine the association of AD with serum tHcy, folate and vitamin $B_{12}$; secondly, to determine whether this association is independent of ApoE ε4; and, thirdly, to assess whether the association could be casual.

In addition, a study was carried out to assess if differences in tHcy levels at recruitment into the study were related to the subsequent rate of disease progression by using atrophy of the medial temporal lobe as a surrogate marker of disease progression.

Methods

Subjects. Between 1988 and 1996, 228 patients with varying degrees of mental deterioration were referred to the Oxford Project to Investigate Memory and Aging (OPTIMA). Included in the present study are the first 76 deceased cases with a histopathological diagnosis of AD and the 88 living cases with a clinical diagnosis of dementia of Alzheimer's type (DAT). Histopathological diagnosis of AD was made using CERAD criteria[4] for "definite or probable AD" and of "not-AD" for patients who were either negative or possible on CERAD criteria. Clinical diagnosis was made using NINCDS-ADRDA criteria [15] of possible or probable DAT and was based on all the information available at the time of analysis of these results.

The 108 controls, who were cognitively normal elderly volunteers from the same community (17 of whom were patient's relatives), were recruited over the same period. All subjects underwent a detailed clinical and psychiatric history, physical examination, assessment of cognitive function (CAMDEX,[16] from which the CAMCOG and MMSE scores were derived) and X-ray cranial computed tomography (CT) scans[17] annually until necropsy. Subject and informant sections of the CAMDEX questionnaire[16] were used for cases and just the subject section for controls. A Dementia Severity Rating score was derived form the severity classification in the CAMDEX, graded at the time of assessment, as follows: none, 0; minimal, 0.5; mild, 1; moderate, 2; severe, 3.

Biochemical measurements.

At the subject's first presentation blood was taken in the non-fasting state, serum and clots for DNA analysis were separated within 4 hours of venepuncture; aliquots were stored at −70° C. Vitamin $B_{12}$ was measured using a radioimmunoassay; serum folate and red-cell folate were determined by bioassays. ApoE genotypes were determined by standard techniques[18] and the 677C-T mutation in the methylenetetrahydrofolate reductase (MTHFR) gene was determined by the procedure of Frosst et al.[19] tHcy analyses were carried out using a HPLC method and fluorescence detection as previously described.[20] Samples from individuals were analyzed in batches and quality control samples were inserted at every 18th sample. The coefficient of variation in the tHcy assays was less than 5% and replicate assays were carried out in samples with tHcy either >40 μmol/l or <4 μmol/l. The self-correlation of tHcy between replicate samples taken at 2 monthly intervals on 7 occasions within one year in 100 healthy elderly UK subjects was 0.87 (unpublished observations).

Statistical analyses.

Mean values of clinical and biochemical variables between cases and controls were compared using an unpaired t-test or Mann-Whitney test, where appropriate; a $X^2$ test was used to assess differences in proportions. Correlations were carried out using a Pearson or Spearman test. The odds ratio for AD was examined using logistic regression for the top third compared to the bottom third of the tHcy concentration in the control population, and vice versa for folate and vitamin $B_{12}$. In the regression models, age was entered as a continuous variable, and remaining confounders such as sex, social class (manual/non-manual), cigarette smokers (current/non-smokers) and ApoE ε4 allele status (present/absent) were entered as dichotomous variables. The confidence intervals for each relative risk were estimated by treating these as "floating absolute risks".[21] The floating absolute risks produce no change in the odds ratio estimates but the variances of those relative risks that are not identically equivalent to 1.0 are reduced by taking account of the variance in the reference category.

Results

Characteristics of the study populations (Table 1)

Patients with confirmed AD were, on average older and of a lower social class than the controls, but were well matched for sex and prevalence of current cigarette use. The disease severity among the AD patients is reflected by the low cognitive scores. 57% of the confirmed AD cases had a Dementia Severity Rating score (Max 3) of 2 or greater at presentation. All subjects had a CT scan at their first visit; 77% of the confirmed AD cases and 12% of the controls had a minimum medial temporal lobe thickness of less than the 5th centile.[17] 25% of the cases were resident in institutions at presentation. There was no significant difference in the history of heart attacks, stroke, or hypertension between cases and controls.

Serum homocysteine

Figure 2:
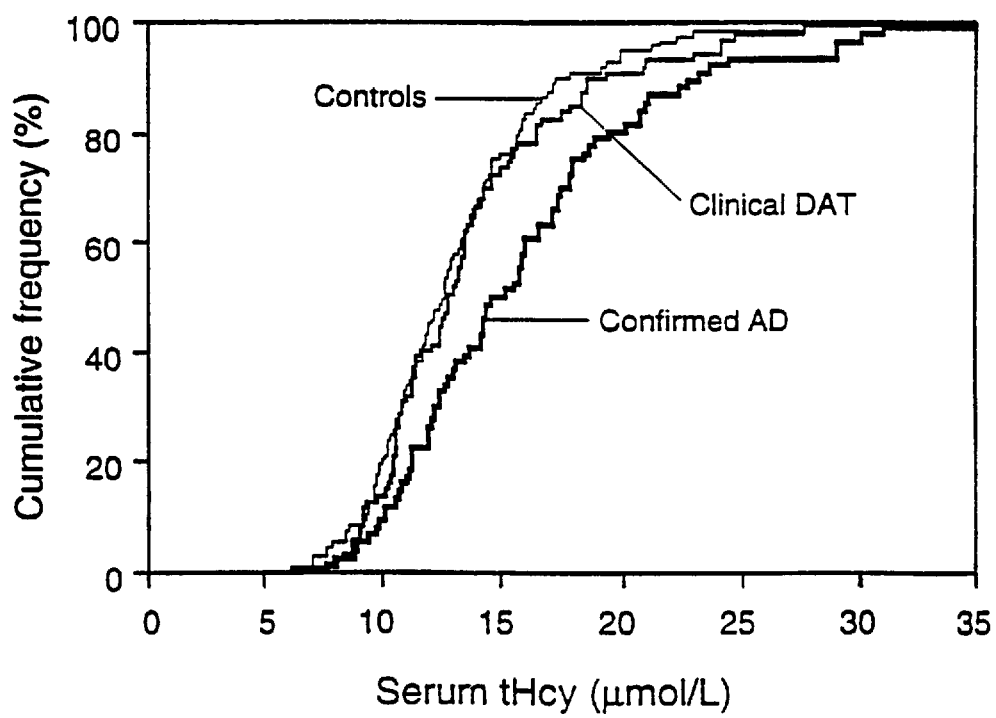

Cumulative frequency plots (FIG. 2) show a shift in the distribution of tHcy concentrations in AD cases to higher values compared with controls. 59% of patients with confirmed AD had a tHcy value in the top third ($\geq 14$ μmol/l) of the control distribution. The mean concentration of tHcy in AD cases was significantly higher than in controls (Table 1). Among controls, tHcy was positively correlated with age (r=0.32; p=0.001), male sex (r=0.27; 0.004), cigarette smoking (r=0.23; p=0.02) and with creatinine (r=0.44; p=0.000) and was inversely associated with serum folate (r=−0.34; p=0.001), vitamin $B_{12}$ (−0.32; p=0.002) and red-cell folate (r=0.21; p=0.048). There was no association between tHcy and either ApoE ε4 or the MTHFR polymorphism in the controls.

Table 2 shows that after controlling for possible confounding due to differences in smoking and social class, there was a 3.8 fold (95% Cl: 2.1–6.9) increased risk of AD associated with the top compared with bottom third of control values of tHcy. The association of thcy with AD was independent of the effect of ApoE ε4, with an odds ratio 4.5 fold (95% Cl: 2.2–9.2) after adjustment for ε4 status. The association between tHcy and AD was attenuated, although it remained significant, after the inclusion of either serum folate, or serum vitamin $B_{12}$ alone or combined in the regression model.

Serum folate and vitamin $B_{12}$

There was a marked shift in the distribution of folate concentrations to lower values in confirmed AD cases compared with controls (FIG. 1). 76% of confirmed AD cases had serum folate concentrations in the bottom third of the control distribution. There was a 5.0 fold (95% Cl: 3.1–8.2) increased risk of AD associated with a serum folate value in the bottom third compared with the top third of the population. Among the controls serum folate levels were lower in current cigarette smokers compared with non-smokers (p<0.05) and, after adjustment for differences due to smoking and social class, there was an attenuation in the strength of the association of serum folate with AD but, as with thcy, this association remained independent of the effect of ApoE ε4 (Table 2). The odds ratios for confirmed AD associated with red-cell folate were similar to those for serum folate (data not shown). For both tHcy and folate the principal difference between cases and controls was in the proportion of subjects in the most extreme tertile (highest tertile for tHcy and lowest tertile for folate). For vitamin $B_{12}$ a similar quantitative difference was seen for the middle as well as for the lowest tertile. The overall strength of association between vitamin $B_{12}$ levels and confirmed AD in the multivariate model was similar to that for tHcy, with an adjusted odds ratio of 4.3 (95% Cl: 2.1–8.8) (Table 2). The risk associations between AD and both serum folate and vitamin $B_{12}$ were no longer significant after the inclusion of tHcy and other confounders in the multivariate model (data not shown).

ApoE and MTHFR polymorphisms

The ApoE ε4 allele frequency among confirmed AD cases was 44% compared with 15% in controls. After Adjusting for differences in age, sex, smoking and social class, the odds ratio of AD for the presence of one or more ApoE ε4 alleles compared with those who had none was 7.9 (95% Cl: 3.3–18.8). The effect of ApoE ε4 was independent of homocysteine as the odds ratio of AD was 9.8 (95% Cl: 3.8–25.5) after the further inclusion of tHcy in the multivariate model. There was no significant difference in the prevalence of the MTHFR gene 677C-T mutation, whether expressed as the proportion homozygous (5% vs 9%) or as allele frequency (22% vs 30%), in confirmed AD cases compared with controls.

Influence of duration of memory impairment

To assess whether the duration of dementia could explain the observed biochemical changes, 72 confirmed AD cases with available data were classified by tertiles of duration of memory impairment (as reported by an informant) prior to their first visit when the blood samples were taken (Table 3). Severity of disease increased substantially during short-term follow-up for several years, but there was no significant trend in the mean levels of any of the biochemical variables with increasing duration of symptoms.

Clinically diagnosed dementia of Alzheimer's type

Within the cohort of 127 living patients, 88 cases had clinically diagnosed DAT. DAT cases were younger than control (70.3 vs 72.8 years; p<0.05). The differences in cognitive scores (CAMCOG score: 64, SD 23; MMSE score: 19, SD 7) were less marked than in confirmed AD cases and the dementia severity was lower (only 21% of the DAT cases had a score of 2 or more compared with 57% of the confirmed AD cases).

There was no significant difference in mean tHcy concentrations (14.3 SD 9.1 vs 13.2 SD 4.0 μmol/l; p=0.23) between the clinically diagnosed DAT cases and controls. The cumulative frequency distribution shows a slight excess of DAT cases with particularly high levels of tHcy (FIG. 2) but the odds ratio of DAT for the upper tertile versus the bottom tertile was 1.1 (95% Cl: 0.6–2.2). DAT cases had lower median serum folate values than controls (7.8 vs 9.1 ng/l; p<0.03). There was a 1.8 (95% Cl: 1.1–3.1) fold increased risk of DAT associated with serum folate concentrations in the bottom compared with the top third of the controls, after adjustment for age, sex, social class and cigarette smoking. Cumulative frequency distribution plots of serum folate concentrations showed that over the entire range, a greater proportion of DAT cases than of controls had low values (FIG. 1). The apoE ε4 allele frequency was 33% in the DAT cases compared with 44% in confirmed AD and 15% in controls. The MTHFR homozygous mutant status did not differ between DAT and AD cases tHcy levels at presentation and disease progression during follow-up To see whether tHcy levels at presentation might be related to the rate of progression of confirmed AD, as assessed by the rate of medial temporal lobe atrophy,[17] serial annual CT scans at follow-up were compared with scans made at presentation in the cohort of 155 clinically diagnosed DAT cases (Table 4). At presentation, the mean age-corrected thickness of the medial temporal lobe for subjects in each of the tertiles of tHcy did not differ. However, three years after the initial scan, medial temporal lobes were significantly thinner in cases with tHcy levels in the middle and upper tertiles compared with those in the lower tertile who showed no atrophy (Table 4).

Discussion

Discovery of a protective factor that could lead to the avoidance or amelioration of AD would certainly be worthwhile if it could be established reliably. The above results show association of histologically confirmed AD with moderately elevated concentrations of tHcy and with moderately lowered blood concentrations of folate and vitamin $B_{12}$ The odds ratio of confirmed AD associated with a tHcy concentration in the top third compared with the bottom third in the controls was 4.5 (95% Cl: 2.2–9.2). The risk associated with tHcy was independent of the risk associated with ApoE ε4.

Replication and earlier studies

Serum folate concentrations were significantly lower in clinically diagnosed DAT cases, with a clear shift in the distribution to lower levels (FIG. 1). However, there were no significant differences in tHcy values or in vitamin $B_{12}$ values between DAT cases and controls. Differences in age, disease severity and the lower prevalence of ApoE ε4 (which suggests that the DAT population includes non-AD cases) may partially explain the discrepant findings between the DAT and AD case populations.

Earlier studies have described positive correlations of tHcy and inverse correlations of folate and vitamin $B_{12}$ in association with cognitive impairment.[22] Correlations of low blood folate[23,24] and vitamin $B_{12}$[23–27] with a clinical diagnosis of DAT have been reported in studies from different populations. The major difference between these studies and the present study is that in the present study subjects who subsequently had a histopathological diagnosis of AD were studied, so overcoming the well known inaccuracies of clinical diagnostic criteria.

Causality and biological plausibility

When patients with confirmed AD were classified by duration of memory impairment before their first visit, the biochemical findings were unaltered by the duration of the illness even though the severity of the dementia increased markedly. This result indirectly supports the view that the observed case-controls differences in tHcy, folate and vitamin $B_{12}$ may be primary, rather than a secondary effect of the disease.

Although the mechanisms underlying the observed associations remain to be established, tHcy is believed to cause vascular disease and the events leading to catastrophic atrophy of the medial temporal lobe might be microvascular in origin. Moreover, homocysteine can be converted into homocysteic acid, which has excitotoxic actions in the nervous system.[28] The association of folic acid and vitamin $B_{12}$ with AD may be mediated through their role in tHcy metabolism, or through their crucial role in methylation reactions in the brain[29] that could involve actions at the level of gene expression[30] or on the stability of DNA.[31,32] It is noteworthy that the gene (presenilin) for the commonest form of familial AD lies in a region (14q24)[33] of chromosome 14 that contains a fragile site revealed by culturing cells in folate-deficient media.[34]

If elevated tHcy levels do affect the development of AD, then supplementation with folic acid and vitamin $B_{12}$ would be an efficient, safe and inexpensive means to reduce them.[35] If these vitamins are protective for AD, then this could be relevant to large populations.

REFERENCES

1. Bowen, D. M, White, P., Spillane, J. A., et al. Accelerated aging or selective neuronal loss as an important cause of dementia? Lancet 1979; i: 11–14.
2. Wischik, C. M., Harrington, C. R., Mukaetova-Ladinska, E. Molecular characterization of the neurodegenerative changes which distinguish normal aging from Alzheimer's disease. In: Huppert, F. A., C. A. B, O'Connor, D. W., eds. Dementia and normal aging. Cambridge: Cambridge University Press, 1994: 470–491.
3. West, M. J., Coleman, P. D., Flood, D. G., Troncoso, J. C. Differences in the pattern of hippocampal neuronal loss in normal aging and Alzheimer's disease. Lancet 1994; 344: 769–772.
4. Jobst, K. A., Smith, A. D., Szatmari, M., et al. Rapidly progressing atrophy of medial temporal lobe in Alzheimer's disease. Lancet 1994; 343: 829–830.
5. Ball, M. J., Hachinski, V., Fox, A., et al. A new definition of Alzheimer's disease: a hippocampal dementia. Lancet 1985; i: 14–16.
6. Schmidt-Kastner, R., Freund, T. F. Selective vulnerability of the hippocampus in brain ischemia. Neuroscience 1991; 40: 599–636.
7. Kalaria, R. N. The blood brain barrier and cerebral microcirculation in Alzheimer disease. Cerebrovasc. Brain Metab. Rev. 1992; 4: 226–260.
8. de la Torre, J. C., Mussivand, T. Can disturbed brain microcirculation cause Alzheimer's disease. Neurol Res 1993; 15: 146–153.
9. Buee, L., Hof, P. R., Bouras, C., et al. Pathological alterations of the cerebral microvasculature in Alzheimer's disease and related dementing disorders. Acta Neuropathol, Berl 1994; 87: 469–480.
10. Roses, A. D. On the metabolism of apolipoprotein E and the Alzheimer diseases. Exp Neurol 1995; 132: 149–156.
11. Boushey, C. J., Beresford, S. A., Omenn, G. S., Motulsky, A. G. A quantitative assessment of plasma homocysteine as a risk factor for vascular disease. Probable benefits of increasing folic acid intakes. J Am Med Assocn 1995; 274: 1049–57.
12. Mills, J. L., McPartlin, J. M. Kirke, P. N., et al. Homocysteine metabolism in pregnancies complicated by neural-tube defects. Lancet 1995; 345: 149–51.
13. Nygard, O., Vollset, S. E., Refsum, H., et al. Total plasma homocysteine and cardiovascular risk profile. The Hordaland Homocysteine Study. J Am Med Assocn 1995; 274: 1526-33.
14. Mirra S. S., Heyman, A., McKeel, D., et al. The Consortium to Establish a Registry for Alzheimer's Disease (CERAD). 2. Standardization of the neuropathologic assessment of Alzheimer's disease. Neurology 1991; 41: 479–486.
15. McKhann, G., Drachman, D., Folstein, M., Katzman, R., Price D., Stadlan, E. M. Clinical diagnosis of Alzheimer's disease: report of the NINCDS-ADRDA work group under the auspices of the Department of Health and Human Services Task Force of Alzheimer's disease. Neurology 1984; 34: 939–944.
16. Roth, M., Huppert, F. A., Tym, E., Mountjoy, C. Q. CAMDEX: The Cambridge examination for mental disorders of the elderly. Cambridge: Cambridge University Press, 1988.
17. Smith, A. D., Jobst, K. A. Use of structural imaging to study the progression of Alzheimer's disease. Brit Med Bull 1996; 1996: 575–586.
18. Wenham, P. R., Price, W. H., Blandell, G. Apolipoprotein E genotyping by one-stage PCR. Lancet 1991; 337: 1158–1159.
19. Frosst, P., Blom, H. J., Milos, R., et al. A candidate genetic risk factor for vascular disease: a common mutation in methylenetetrahydrofolate reductase. Nat Genet 1995; 10: 111-3.
20. Ueland, P. M., Refsum, H., Stabler, S. P., Malinow, M. R., Andersson, A., Allen, R. H. Total homocysteine in plasma or serum: methods and clinical applications. Clin Chem 1993; 39: 1764-79.
21. Easton, D. F., Peto, J., Babiker, A. G. Floating absolute risk: an alterntive to relative risk in survival and case-control analysis avoiding an arbitrary reference group. Stat Med 1991; 10: 1025-35.
22. Riggs, K. M., Spiro, A., Tucker, K., Rush, D. Relations of vitamin B-12, vitamin B-6, folate, and homocysteine to cognitive performance in the Normative Aging Study. Am J Clin Nutr 1996; 63: 306–314.
23. Renvall, M. J., Spindler, A. A., Ramsdell, J. W., Paskvan, M. Nutritional status of free-living Alzheimer's patients. Am J. Med Sci 1989; 298: 20-7.
24. Kristensen, M. O., Gulmann, N. C. Christensen J. E. J., Ostergaard, K., Rasmussen, K. Serum cobalamin and methylmalonic acid in Alzheimer dementia. Acta Neurol Scand 1993; 87: 475–481.
25. Cole, M. G. Prchal, J. F. Low serum vitamin $B_{12}$ in Alzheimer-type dementia. Age Ageing 1984; 13: 101-5.
26. Karnaze, D. S., Carmel, R. Low serum cobalamin levels in primary degenerative dementia. Do some patients harbor atypical cobalamin deficiency states? Arch Intern Med 1987; 147: 429-31.

27. Nijst, T. Q., Wevers, R. A., Schoonderwaldt, H. C., Hommes, O. R., de Haan, A. F. Vitamin $B_{12}$ and folate concentrations in serum and cerebrospinal fluid of neurological patients with special reference to multiple sclerosis and dementia. J. Neurol Neurosurg Psychiatry 1990; 53: 951-4.
28. Beal, M. F., Swartz, K. J., Finn, S. F., Mazurek, M. F., Kowall, N. W. Neurochemical characterization of excitotoxin lesions in the cerebral cortex. J Neurosci 1991; 11: 147-58.
29. Bottiglieri, T., Hyland, K., Reynolds, E. H. The clinical potential of adenosylmethionine (S-adenosyl-methionine) in neurological disorders. Drugs 1994; 48: 137–152.
30. Bird, A. P. Functions for DNA methylation in vertebrates. Cold Spring Harb Symp Quant Biol 1993; 58: 281-5.
31. Mullaart, E., Boerrigter, METI, Ravid, R., Swaab, D. F., Vijg, J. Increased Levels of DNA Breaks in cerebral cortex of Alzheimer's disease patients. Neurobiol Aging 1990; 11: 169–173.
32. Ettinger, S., Weksler, M. E., Zhou, X. T., Blass, J., Szabo, P. Chromosomal fragility associated with familial Alzheimer's disease. Annals of Neurology 1994; 36: 190–199.
33. Clark, R. F., Hutton, M., Fuldner, R. A., et al. The structure of the presenilin 1 (S182) gene and identification of six novel mutations in early onset AD families. Nat Genet 1995; 11: 219–222.
34. Kormann Bortolotto, M. H., Smith, M. D. A., Toniolo Neto, J. Fragile sites, Alzheimer's disease, and aging. Mech Ageing Dev 1992; 65: 9–15.
35. Stampfer, M. J., Rimm, E. B. Folate and cardiovascular disease: why we need a trial now. J Am Med Assocn 1996; 275: 1929-30.

TABLE 1

Distribution of selected variables in controls and in histologically-confirmed Alzheimer's disease cases at presentation.

| Variables<br>Mean (SD) or % | Cases<br>(n = 76) | Controls<br>(n = 108) | p* |
|---|---|---|---|
| Clinical variables | | | |
| Age (years) | 76.6 (8.0) | 72.8 (8.8) | 0.003 |
| Sex (% males) | 37 | 43 | 0.392 |
| Current smokers (%) | 24 | 21 | 0.720 |
| Social class: Grade 1&2 (%) | 49 | 80 | 0.000 |
| CAMCOG score (Max 107) | 45.1 (27.5) | 97.9 (4.9) | 0.000 |
| MMSE score (Max 30) | 12.8 (8.1) | 28.5 (1.7) | 0.000 |
| Minimal medial temporal lobe wall thickness (mm) | 8.2 (2.5) | 12.9 (2.8) | 0.000 |
| Biochemical variables** | | | |
| Homocysteine (μmol/l) | 16.3 (7.4) | 13.2 (4.0) | 0.000 |
| Serum folate (μg/l) | 6.7 (4.2) | 10.1 (4.4) | 0.000 |
| Red-cell folate (μg/l) | 326 (171) | 438 (180) | 0.000 |
| Vitamin $B_{12}$ (ngl/l) | 292 (107) | 343 (135) | 0.015 |
| Creatinine (μmol/l) | 90 (20) | 93 (19) | 0.321 |
| Albumin (g/l) | 42.0 (4) | 45 (4) | 0.000 |
| Haemoglobin (mg/dl) | 13.1 (1.5) | 13.6 (1.5) | 0.021 |

TABLE 1-continued

Distribution of selected variables in controls and in histologically-confirmed Alzheimer's disease cases at presentation.

| Variables<br>Mean (SD) or % | Cases<br>(n = 76) | Controls<br>(n = 108) | p* |
|---|---|---|---|
| Genotypes | | | |
| ApoE ε4 allelle frequency (%) | 44 | 14 | 0.000 |
| MTHFR homozygous mutant frequency*** (%) | 5 | 9 | 0.243 |

*p was assessed using a unpaired t-test for continuous values and a $x^2$ test for proportions.
**Data on folate, and vitamin $B_{12}$ was available in 62 cases and in 92 controls.
***MTHFR denotes Methylenetetrahydrofolate reductase.

TABLE 2

Odds ratio or "floating absolute risk" (95% Cl) of histologically confirmed Alzheimer's disease compared with controls for each tertile of plasma total homocysteine and of serum folate*.

| | Odds ratio or "floating absolute risk" (95% Cl) | | |
|---|---|---|---|
| Tertiles of homocysteine & folate | Adjusted for age & sex | Adjusted for age, sex, smoking & social class | Adjusted for age, sex, smoking, social class & apo ε4 |
| Homocysteine (μmol/l) | | | |
| I  ≤11.0 | 1.0 (0.5–1.9) | 1.0 (0.4–2.4) | 1.0 (0.4–2.7) |
| II  11.1 ≤ 14.0 | 1.3 (0.7–2.3) | 1.5 (0.7–3.1) | 1.0 (0.4–2.3) |
| III  >14.0 | 3.3 (2.1–5.2) | 3.8 (2.1–6.9) | 4.5 (2.2–9.2) |
| Serum folate (μg/l) | | | |
| III  >10.7 | 1.0 (0.5–2.1) | 1.0 (0.4–2.6) | 1.0 (0.3–3.1) |
| II  7.6 ≤ 10.7 | 0.6 (0.2–1.6) | 0.6 (0.2–2.0) | 0.4 (0.1–1.5) |
| I  ≤7.5 | 5.0 (3.1–8.2) | 4.1 (2.3–7.3) | 3.3 (1.8–6.3) |
| Serum vitamin $B_{12}$ (ng/l) | | | |
| III  >380 | 1.0 (0.5–2.10) | 1.0 (0.3–3.1) | 1.0 (0.3–3.8) |
| II  271 ≤ 380 | 2.1 (1.2–3.6) | 3.5 (1.8–6.6) | 5.6 (2.6–11.9) |
| I  ≤270 | 1.8 (1.0–3.2) | 2.9 (1.4–5.7) | 4.3 (2.1–8.8) |

*Use of "floating absolute risks" does not alter the odds ratios, but when due account is taken of the effects of the play of chance on the odds of disease in the reference category (thereby effectively attributing a variance to the odds ratio of 1.0 in this category) then the variance attributed to the other two odds ratios are reduced.

TABLE 3

Selected clinical and biochemical variables in those with histologically confirmed Alzheimer's disease (n = 72) according to the duration of memory impairment at presentation as reported by an informant.

| Tertiles of duration of memory impairment (years) | Clinical variables [Mean(SD) or %] | | | Biochemical variables [mean (SD)] | | | |
|---|---|---|---|---|---|---|---|
| | MMSE score (Max 30) | Min. medial temporal lobe thickness (mm) | Dementia severity rating (Max 3) %2 or 3 | Homocysteine ($\mu$mol/l) | Plasma folate (ug/l) | Red-cell folate (ng/l) | Vit $B_{12}$ (ng/l) |
| I <2 | 16 (8) | 9.0 (2.4) | 33% | 18.8 (10.8) | 7.8 (5.4) | 331 (206) | 293 (111) |
| II 2–4 | 14 (8) | 8.7 (4.8) | 56% | 15.4 (5.7) | 5.7 (2.5) | 319 (176) | 273 (85) |
| III >4 | 8 (6) | 7.1 (4.3) | 88% | 14.8 (4.1) | 6.2 (3.2) | 312 (107) | 320 (121) |
| test for linear trend:p | 0.00 | 0.00 | 0.00 | 0.06 | 0.19 | 0.72 | 0.42 |

TABLE 4

The annual change in medial temporal lobe thickness (MMTL) as assessed on CT, in cases with a clinical diagnosis of dementia of Alzheimer's type (DAT), who at baseline were classified by tertiles of total monocysteine (tHcy) in the controls.

| | Mean (SD)MMTL values at baseline (n = 155) | | | Mean age-adjusted MMTL values[†] relative to baseline (%) | | | |
|---|---|---|---|---|---|---|---|
| | No. of cases | Absolute values (mm) | Age adjusted[†] values (%) | Year 0 (n = 155) | Year 1 (n = 108)[‡] | Year 2 (n = 66)[‡] | Year 3 (n = 42)[‡] |
| tHcy at baseline ($\mu$mol/l) | | | | | | | |
| I ≦11 | 39 | 9.7 (2.5) | 0.71 (0.18) | 100 | 102 | 94 | 97 |
| II 11.1 ≦ 14.0 | 45 | 9.5 (2.7) | 0.70 (0.18) | 100 | 92 | 76 | 70 |
| III >14.0 | 71 | 8.7 (2.5) | 0.66 (0.19) | 100 | 94 | 88 | 81 |
| Test for difference by tertiles of tHcy[§] | | 0.09 | 0.31 | | 0.20 | 0.04 | 0.04 |

[†]Details of how the age-adjusted values were derived having been previously described.[16]
[‡]Subset with available measurements.
[§]ANOVA, Prob > F

What is claimed is:

1. A method for treating Alzheimer's disease or inhibiting microvascular events leading to neurodegeneration, which comprises administering to a patient in need of treatment a therapeutically effective amount of a drug which causes a reduction in at least moderately elevated blood levels of homocysteine or modifies the toxic effects of at least moderately elevated blood levels of homocysteine on the vasculature or on nerve cells in the brain, wherein the drug employed is a nitric oxide donor, a NEP/ACE inhibitor, an ACE inhibitor or angiotensin II antagonist, betaine or vitamin $B_6$ or a combination of two or more thereof, or a combination of any one or more of the above with folic acid, a folate or a derivative thereof.

2. A method for treating Alzheimer's disease, which comprises administering to a patient in need of treatment a therapeutically effective amount of a drug which causes a reduction in at least moderately elevated blood levels of homocysteine or modifies the toxic effects of at least moderately elevated blood levels of homocysteine on the vasculature or on nerve cells in the brain, wherein the drug employed is a nitric oxide donor, a NEP/ACE inhibitor, an ACE inhibitor or angiotensin II antagonist, betaine or vitamin $B_6$ or a combination of two or more thereof, or a combination of anyone or more of the above with folic acid, a folate or a derivative thereof.

3. The method as defined in claim 2 wherein the patient has at least moderately elevated blood levels of homocysteine and at least moderately reduced blood levels of folate and vitamin $B_{12}$.

4. The method as defined in claim 2 wherein the drug administered is a combination of two or more of folic acid or a folate or a derivative thereof, and betaine or vitamin $B_6$.

5. The method as defined in claim 4 wherein the drug is folic acid, one or more of the folylpolyglutamates, compounds in which the pyrazine ring of the pterin moiety of folic acid or of the folylpolyglutamates is reduced to give dihydrofolates or tetrahydrofolates, or derivatives of all the preceding compounds in which the N-5 or N-10 positions carry one carbon unit at various levels of oxidation, or a combination of two or more thereof.

6. The method as defined in claim 5 wherein the folic acid, folate or derivative thereof is folic acid,
dihydrofolate,
tetrahydrofolate,
5-methyltetrahydrofolate,
5,10-methylenetetrahydrofolate,
5,10-methenyltetrahydrofolate,
5,10-formiminotetrahydrofolate,
5-formyltetrahydrofolate (leucovorin),
10-formyltetrahydrofolate, or a combination of two or more thereof.

7. The method as defined in claim 3 further including the step of administering vitamin $B_{12}$.

8. The method as defined in claim 2 wherein said angiotensin converting enzyme inhibitor is captopril, fosinopril, lisinopril, enalapril, ramipril, quinapril, fentiapril, benazepril or moexipril and said angiotensin II antagonist is irbesartan or losartan.

9. The method as defined in claim 2 wherein said nitric oxide donor is isosorbide mononitrate or isosorbide dinitrate or nitroglycerin.

10. The method as defined in claim 2 wherein the drug administered is a combination of an ACE inhibitor or angiotensin II antagonist, and folic acid, a folate or a derivative thereof.

11. The method as defined in claim 10 wherein the drug is a combination of (a) captopril, fosinopril or irbesartan, and (b) folic acid, a folate or a derivative thereof.

12. The method as defined in claim 2 wherein folic acid, folate or a derivative thereof or betaine or vitamin $B_6$ is administered in a daily dosage within the range from about 0.1 to about 100 mg.

13. The method as defined in claim 2 wherein vitamin $B_{12}$ is administered in a daily dosage within the range from about 0.001 to about 10 mg.

14. The method as defined in claim 2 further including administering a drug for treating Alzheimer's disease which is a cholinesterase inhibitor, a muscarinic receptor agonist, an inhibitor of β-amyloid production, an inhibitor of neurofibrillary tangle formation or a combination of two or more thereof.

15. A pharmaceutical combination comprising
(1) folic acid, a folate or a derivative thereof, or betaine or vitamin $B_6$ or a combination of two or more thereof;
(2) vitamin $B_{12}$; and
(3) a nitric oxide donor, an ACE inhibitor, or an angiotensin II antagonist, or a NEP/ACE inhibitor, or a combination of two or more thereof or a cholinesterase inhibitor, a muscarinic receptor agonist, an inhibitor of β-amyloid production, an inhibitor of neurofibrillary tangle formation or a combination of two or more thereof.

16. The combination as defined in claim 15 comprising folic acid or a folate and fosinopril or captopril or irbesartan.

* * * * *